United States Patent [19]

Krzysik

[11] Patent Number: 5,869,075
[45] Date of Patent: Feb. 9, 1999

[54] SOFT TISSUE ACHIEVED BY APPLYING A SOLID HYDROPHILIC LOTION

[75] Inventor: Duane Gerard Krzysik, Appleton, Wis.

[73] Assignee: Kimberly-Clark Worldwide, Inc., Neenah, Wis.

[21] Appl. No.: 911,253

[22] Filed: Aug. 15, 1997

[51] Int. Cl.$^6$ .............................. A01N 25/34; A61K 6/00; A61K 7/00

[52] U.S. Cl. ........................................... 424/414; 424/401

[58] Field of Search ....................................... 424/401, 414

[56] References Cited

U.S. PATENT DOCUMENTS

| | | | |
|---|---|---|---|
| 5,558,873 | 9/1996 | Funk et al. | 424/401 |
| 5,653,989 | 8/1997 | Sattler | 424/401 |
| 5,665,426 | 9/1997 | Krzysik et al. | 427/211 |

OTHER PUBLICATIONS

American Society for Testing Materials (ASTM) Designation: D 1321–92, "Standard Test Method for Needle Penetration of Petroleum Waxes," pp. 483–485, published Dec. 1992.

*Primary Examiner*—Leonard Schenkman
*Attorney, Agent, or Firm*—Gregory E. Croft

[57] ABSTRACT

A superior soft tissue product, such as facial tissue, bath tissue or paper towels and the like, can be made applying, on the surface(s) of the tissue, large numbers of individual deposits of a melted hydrophilic composition comprising a high molecular weight polyethylene glycol, a fatty alcohol ($C_{14}$–$C_{30}$) and lipophilic emollients or solvents, including water, and thereafter resolidifying the composition to form a distribution, preferably a uniform distribution, of solid deposits on the surface(s) of the tissue. Because the composition is a solid at room temperature and rapidly solidifies after deposition, it has less tendency to penetrate and migrate into the sheet. These solid deposits are characterized by a penetration hardness of from about 5 to about 360 millimeters.

33 Claims, No Drawings

SOFT TISSUE ACHIEVED BY APPLYING A SOLID HYDROPHILIC LOTION

BACKGROUND OF THE INVENTION

Absorbent tissue products such as facial tissue and bath tissue have been used to absorb body fluids and leave the skin dry. Absorbent tissue, in addition to absorbing fluids, however, also abrade the skin during use and frequently do not leave the skin completely dry and free of the body fluid the tissue is trying to absorb. During frequent nose-blowing or perianal wiping, the skin can become so abraded as to appear red and be sore to the touch. To reduce skin abrasion, tissue additive formulations can be applied to the tissue such that, in use, the additive formulation either provides lubricity causing the tissue to glide across the surface of the skin, or leaves the tissue and is deposited on the skin. To date, these formulations have been liquids or lipid (lipophilic materials) based semi-solids or lipid based solids at room temperature. The liquid or lipid-based semi-solid type of formulations require a high amount of formulation added to the tissue to deliver the benefit of reduced skin irritation and redness because these formulations absorb into a tissue, leaving less on the surface to provide the benefit. The lipid based solid formulations can be applied heated (slightly above the melting point of the formulation) to the surface of a tissue or towel thereafter resolidifying the formulation on the surface (s) of the tissue where the formulation is readily available for transfer to the users skin to protect the skin from or prevent further irritation and redness in an efficient cost-effective manner. However, since these formulations are lipophilic it is sometimes difficult to incorporate hydrophilic or water soluble surfactants, cosmetic materials or active ingredients.

Thus, there is a need for a formulation that is basically hydrophilic and can be applied to a tissue which will remain readily available for transfer to the user's skin to protect the skin from or further irritation and redness in an efficient cost-effective manner.

SUMMARY OF THE INVENTION

It has now been discovered that a superior soft tissue product can be made applying, on the surface(s) of the tissue, large numbers of individual deposits of a melted hydrophilic composition comprising a high molecular weight polyethylene glycol, a fatty alcohol ($C_{14}$–$C_{30}$) and lipophilic emollients or solvents including water, and thereafter resolidifying the composition to form a distribution, preferably a uniform distribution, of solid deposits on the surface(s) of the tissue. Because the composition is a solid at room temperature and rapidly solidifies after deposition, it has less tendency to penetrate and migrate into the sheet. Compared to tissues treated with liquid formulations, this leaves a greater percentage of the added composition on the surface of the tissue where it can contact and transfer to the user's skin to provide a benefit. Furthermore, a lower add-on amount can be used to deliver the same benefit at a lower cost because of the efficient placement of the composition substantially at the surface of the product.

Hence in one aspect, the invention resides in a softening composition comprising from about 30 to about 90 weight percent hydrophilic solvent, from about 10 to about 50 weight percent high molecular weight polyethylene glycol having a molecular weight of about 720 or greater, and from about 5 to about 40 weight percent of a $C_{14}$ to $C_{30}$ fatty alcohol, said composition having a melting point from about 30° C. to about 700° C. and a penetration hardness of from about 5 millimeters to 360 millimeters.

In another aspect, the invention resides in a tissue product wherein one or both of the outer surfaces of the product have solidified deposits of a composition comprising from about 30 to about 90 weight percent hydrophilic solvent, from about 10 to about 50 weight percent of a high molecular weight (defined as a solid at room temperature) polyethylene glycol and from about 5 to about 40 weight percent fatty alcohol, said composition having a melting/freezing point of from about 30° C. to about 70° C. and a penetration hardness from about 5 millimeters of penetration to 360 millimeters of penetration.

In another aspect, the invention resides in a method of making a soft tissue or towel product comprising: (a) heating a composition comprising a hydrophilic solvent, high molecular weight polyethylene glycol and a fatty alcohol, to a temperature above the melting point of the composition, causing the composition to melt, said composition having a melting point of from about 30° C. to about 70° C.; (b) uniformly applying the melted composition to one or both surfaces of the tissue web in spaced-apart deposits; and (c) resolidifying the deposits of the melted composition. Resolidification of the deposits can occur almost instantaneously, without the need for external cooling means such as chill rolls, if the composition is heated to a temperature only slightly above or at the melting point of the composition. However, external means such as chill rolls, either before or after the application of melt, can be used if desired to accelerate resolidification. Such instantaneous resolidification tends to impede penetration of the composition into the tissue and retain it on the surface of the tissue, which is advantageous. For example, the temperature of the melted composition can advantageously be above the melting point about 10° C. or less, more specifically about 5° C. or less and still more specifically about 2° C. or less. As the temperature of the melted composition approaches the melting point, the viscosity of the melted composition generally increases, which further enhances the tendency of the melted composition to be retained on the surface.

For purposes herein, "melting point" is the temperature at which the majority of the melting occurs, it being recognized that melting actually occurs over a range of temperatures. The melting point of the compositions of this invention can be from about 30° C. to about 70° C., more specifically from about 40° C. to about 70° C., and still more specifically from about 50° C. to about 60° C.

In addition, for purposes herein, "penetration hardness" is the needle penetration in millimeters according to ASTM D 1321, "Needle Penetration of Petroleum Waxes. Lower needle penetration hardness values correspond to harder materials. The penetration hardness of the compositions of this invention can be from about 5 to 360 millimeters, more specifically from about 5 to about 200 millimeters, more specifically from about 5 to about 150 millimeters, and still more specifically from about 5 to about 100 millimeters. (Formulations having a needle penetration hardness greater than 360 millimeters cannot be measured using ASTM method D 1321). The hardness of the formulations of this invention is important for two reasons. First, the softer the formulation the more mobile the formulation will be, making the formulation more likely to migrate to the inner plies of the tissue, which is not desirable. Secondly, softer formulations tend to be more greasy/oily to the touch, which is also less desirable. In general, formulations having a needle penetration hardness of from about 200 to 360 millimeters feel creamy to slightly greasy with less smoothness (depending on additives). Formulations that have needle penetration hardness values of from about 5 to about 200 millimeters feel silky to creamy and very smooth (depending on additives).

The amount of hydrophilic solvent, including water if present, can be from about 30 to about 90 weight percent, more specifically from about 40 to about 70 weight percent, more specifically from about 50 to about 60 weight percent. As used herein, suitable hydrophilic solvents include, but are not limited to, the following materials: water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol, hydrogenated starch hydrolysate, and silicone glycols.

The amount of high molecular weight polyethylene glycol in the composition can be from about 10 to about 50 weight percent, more specifically from about 10 to about 30 weight percent, and still more specifically from about 15 to about 25 weight percent. As used herein, high molecular weight polyethylene glycols are polyethylene glycols having an average molecular weight of 720 or greater. These materials are not liquid at room temperature. Particularly suitable high molecular weight polyethylene glycols can have an average molecular weight of from 720 to about 1,840,000, more specifically from about 1400 to about 440,000, and still more specifically from about 1760 to about 10,570.

The amount of fatty alcohol in the composition can be from about 5 to about 40 weight percent, more specifically from about 10 to about 30 weight percent, and still more specifically from about 15 to 25 weight percent. Suitable fatty alcohols include, but are not limited to, alcohols having a carbon chain length of $C_{14}$–$C_{30}$, including cetyl alcohol, stearyl alcohol, arachidyl alcohol, and behenyl alcohol.

In order to better enhance the benefits to consumers, additional ingredients can be used. The classes of ingredients and their corresponding benefits include, without limitation: antiacne actives (a drug product used to reduce the number of acne blemishes, acne pimples, blackheads, and whiteheads); antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); humectants (increase the water content of the top layers of the skin); natural moisturizing agents (NMF) and other skin moisturizing ingredients known in the art; opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); solvents (liquids employed to dissolve components found useful in the cosmetics or drugs); sunscreens (ingredients that absorb at least 85 percent of the light in the UV range at wavelengths from 290 to 320 nonometers, but transmit UV light at wavelengths longer than 320 manometers); and surfactants (as cleansing agents, emulsifying agents, solubilizing agents, and suspending agents).

In addition, to these classes of ingredients, from about 0.01 to about 20 weight percent of oil soluble/dispersible or lipophilic materials can be easily emulsified into the formulation using anionic, amphoteric, cationic, nonionic and/or zwitterionic surfactants. Lipophilic materials without limitation include, silicones/organomodified silicones (protection, tissue water resistance, lubricity, tissue softness); oils (mineral, vegetable, and animal); fatty esters and the like. Powders to enhance lubricity, oil adsorption, provide skin protection, astringency, opacity, etc. and microencapsulated ingredients can also be dispersed into the formulation.

The total tissue add-on of the composition can be from about 0.5 to about 40 weight percent, more specifically from about 5 to about 30 weight percent, and more specifically from about 10 to about 15 weight percent, based on the weight of the tissue. The add-on amount will depend upon the desired effect of the composition on the product attributes and the specific composition. A preferred method to uniformly apply the heated composition to the surface of the tissue web is rotogravure printing, either direct or indirect (offset), because it is the most exact printing process and offers maximum control of the composition distribution and transfer rate. However, other printing methods, such as flexographic printing or spraying such as WEKO, can be used.

As used herein, all recited ranges of amounts, temperatures, molecular weights and penetration hardnesses are intended to include all sub-ranges within the recited ranges, even though not specifically stated.

Also as used herein, a "tissue product" can be a facial tissue, bath tissue, paper towel, dinner napkin or the like. The tissue products of this invention can be one-ply, two-ply, three-ply or more. In all cases, the composition is applied to one or both outer surfaces of the product after the product has been dried. The composition can be applied after the plies are brought together or prior to bringing the plies together. The individual plies can be layered or blended (homogeneous) creped or uncreped, throughdried or wet-pressed. Surprisingly, it had been found that blended tissue basesheets provide equivalent performance to layered basesheets, hence fiber layering is unnecessary.

EXAMPLES

Example 1

A tissue softening formulation (soft, semi-solid jelly) having a penetration hardness greater than 360 millimeters and a melting point about 28° C. was prepared having the following composition:

|   | Weight Percent |
|---|---|
| 1) Propylene Glycol | 40.00 |
| 2) Stearalkonium Chloride 85% | 1.00 |
| 3) Polyethylene Glycol 1000 | 40.00 |
| 4) Glycerin | 19.00 |

The formulation was prepared by heating the propylene glycol to 45°–50° C., adding the stearalkonium chloride and polyethylene glycol 1000 and mixing until melted. Glycerin was then added and mixed until uniform. At this point the formulation was ready to use and apply to a tissue or towel basesheet via rotogravure printing. This formulation is a soft-semi-solid. It was too soft to sit on the surface of the basesheet but provided a softening effect. Glycerin was used in this formulation to provide a moisturization (humectancy) benefit to the skin.

Example 2

A tissue softening formulation (soft, semi-solid jelly) having a penetration hardness of greater than 360 millimeters and a melting point about 29° C. was prepared having the following composition:

|   | Weight Percent |
|---|---|
| 1) Propylene Glycol | 20.00 |
| 2) Stearalkonium Chloride (85%) | 1.10 |
| 3) Polyethylene Glycol 1000 | 40.00 |
| 4) Glycerin | 38.90 |

The formulation was prepared by heating the propylene glycol to 45°–50° C., adding stearalkonium chloride (Mackernium SDC-85 from McIntyre) and polyethylene glycol 1000 and mixing until melted. Glycerin was then added and mix until uniform. At this point the formulation was ready to use and apply to tissue or towel basesheet. This formulation is a soft semi-solid and was applied via flexographic printing at 5 percent of the weight of the tissue to one side of an uncreped through aired dried bath tissue. The bath tissue was very soft. However, due to the semi-solid nature of the formulation, the formulation did not sit on the surface of the basesheet.

Example 3 (Invention)

A tissue softening formulation (soft solid) having a penetration hardness of approximately 170 millimeters and a melting point about 44° C. was prepared having the following composition:

|   | Weight Percent |
|---|---|
| 1) Propylene Glycol | 15.00 |
| 2) Stearalkonium Chloride (75%) | 1.00 |
| 3) Polyethylene Glycol 1000 | 50.00 |
| 4) Cetyl Alcohol | 10.00 |
| 5) Hydrogenated Starch Hydrolysate | 24.00 |

The formulation was prepared by heating the propylene glycol to 45°–50° C., adding the stearalkonium chloride, polyethylene glycol 1000 and cetyl alcohol and mixing until melted. Hydrogenated starch hydrolysate was then added and mixed until uniform. At this point the formulation was ready to use and apply to tissue or towel basesheet via rotogravure printing. The formulation was a soft solid and sat on the surface of the basesheet when applied. The hydrogenated starch hydrolysate was used in this formulation to provide moisturization (humectancy) benefits to the skin and as a low cost alternative to glycerin. It also is not considered to be a volatile organic compound (VOC) like propylene glycol and can be used as a partial replacement for the propylene glycol.

Example 4 (Invention)

A tissue softening formulation (soft solid) having a penetration hardness of approximately 130 millimeters and a melting point about 45° C. was prepared having the following composition:

|   | Weight Percent |
|---|---|
| 1) Propylene Glycol | 15.00 |
| 2) Stearalkonium Chloride (75%) | 1.00 |
| 3) Polyethylene Glycol 1000 | 25.00 |
| 4) Polyethylene Glycol 3350 | 25.00 |
| 5) Cetyl Alcohol | 10.00 |
| 6) Hydrogenated Starch Hydrolysate | 24.00 |

The formulation was prepared by heating the propylene glycol to 45°–50° C., adding the stearalkonium chloride, polyethylene glycols 1000 and 3350 and cetyl alcohol, mixing until melted. Hydrogenated starch hydrolysate was then added and mixed until uniform. At this point the formulation was ready to use and apply to the surface of a tissue or towel basesheet via rotogravure printing. This formulation is a harder solid than those of the foregoing examples due to the use of propylene glycol 3350.

Example 5 (Invention)

A tissue softening formulation (solid) having a penetration hardness of approximately 135 millimeters and a melting point about 57° C. was prepared having the following composition:

|   | Weight Percent |
|---|---|
| 1) Propylene Glycol | 20.00 |
| 2) Stearalkonium Chloride (85%) | 5.00 |
| 3) Polyethylene Glycol 1000 | 25.00 |
| 4) Polyethylene Glycol 8000 | 25.00 |
| 5) Hydrogenated Starch Hydrolysate | 25.00 |

The formulation was prepared by heating the propylene glycol to 50°–55° C., adding the polyethylene glycols 1000 and 8000, mixing until melted. Hydrogenated starch hydrolysate was then added and mixed until uniform. At this point the formulation was ready to use and apply to the surface of a tissue or towel basesheet via rotogravure printing. This formulation is a harder solid than the above examples due to the use of polyethylene glycol 8000.

Example 6 (Invention)

A tissue softening formulation (solid) having a penetration hardness of approximately 94 millimeters and a melting point about 55° C. was prepared having the following composition:

|   | Weight Percent |
|---|---|
| 1) Propylene Glycol | 20.00 |
| 2) Polyethylene Glycol 400 | 10.00 |
| 3) Polyethylene Glycol 1000 | 25.00 |
| 4) Polyethylene Glycol 8000 | 25.00 |
| 5) Hydrogenated Starch Hydrolysate | 20.00 |

The formulation was prepared by heating propylene glycol and polyethylene glycol 400 to 55°–60° C., then adding polyethylene glycols 1000 and 8000, mixing until melted. Hydrogenated starch hydrolysate was then added and mixed until uniform. At this point the formulation was ready to use and apply to the surface of a tissue or towel basesheet via rotogravure printing.

Example 7 (Invention)

A tissue softening formulation (solid) having a penetration hardness of approximately 238 millimeters and a melting point about 50° C. was prepared having the following composition:

|   | Weight Percent |
|---|---|
| 1) Propylene Glycol | 10.00 |
| 2) Polyethylene Glycol 400 | 10.00 |
| 3) Polyethylene Glycol 1000 | 20.00 |
| 4) Polyethylene Glycol 8000 | 30.00 |
| 5) Hydrogenated Starch Hydrolysate | 20.00 |
| 6) Dimethicone Copolyol | 10.00 |

The formulation was prepared by heating propylene glycol and polyethylene glycol 400 to 55°–60° C., adding the polyethylene glycols 1000 and 8000, and mixing until melted. Hydrogenated starch hydrolysate and dimethicone copolyol (Dow Corning 190 surfactant) were added and mixed until uniform. At this point the formulation was ready to use and apply to the surface of the tissue or towel basesheet via rotogravure printing. Dimethicone copolyol was used in this formulation to provide a softer/silkier feel to the surface of the basesheet.

Examples 8 to 10 (Invention)

Tissue softening formulations with various glycol type hydrophilic solvents having a penetration hardness range of approximately 10 to 65 millimeters and an approximate melting point range of 50°–54° were prepared having the following compositions:

|   | 8 Wt % | 9 Wt % | 10 Wt % |
|---|---|---|---|
| 1) Propylene Glycol | 55.00 | — | — |
| 2) Polyethylene Glycol 400 | — | 55.00 | — |
| 3) MPDiol Glycol | — | 20.00 | 55.00 |
| 4) Polyethylene Glycol 8000 | 20.00 | 20.00 | 20.00 |
| 5) Stearyl Alcohol | 20.00 | 20.00 | 20.00 |
| 6) Stearalkonium Chloride | 5.00 | 5.00 | 5.00 |

These formulations were prepared by heating the propylene glycol, polyethylene glycol or MPDiol glycol to 60° C., adding the polyethylene glycol and mixing until melted. ("MPDiol Glycol" is methyl propanediol.) Stearyl alcohol and stearalkonium chloride were added and mixed until melted. At this point the formulation was ready to use and apply to the surface of the tissue or towel basesheet via rotogravure printing.

Examples 11 to 13 (Invention)

Tissue softening formulations containing moisturizing ingredients and feel modifiers having a penetration hardness range of 20 to 130 millimeters and approximate melting point range of 53°–60° C. were prepared having the following compositions:

|   | 11 Wt % | 12 Wt % | 13 Wt % |
|---|---|---|---|
| Phase A |   |   |   |
| 1) Propylene Glycol | 35.00 | 28.00 | 35.00 |
| 2) Polyethylene Glycol 8000 | 20.00 | 15.00 | 20.00 |
| 3) Behenyl Alcohol | 10.00 | 10.00 | 10.00 |
| 4) Stearyl Alcohol | 10.00 | 10.00 | 10.00 |
| 5) Hydrogenated Starch Hydrolysate | — | 15.00 | — |
| 6 A) Hispagel 200 | 10.00 | — | — |
| B) Lubrasil | — | 7.00 | — |
| C) Ostar Arriveen PG25 | — | — | 10.00 |
| Phase B |   |   |   |
| 7) Dimethicone 100 cSt | 10.00 | 10.00 | 10.00 |
| 8) Myristyl Myristate | 5.00 | 5.00 | 5.00 |

"Hispagel 200" is a mixture of glyceryl and glyceryl polyacrylate manufactured by Hispano Quimica S.A. "Lubrasil" is a mixture of glyceryl polymethacrylate, propylene glycol, cyclomethicone, dimethiconol and polysorbate 20 manufactured by United Gardian, Inc. "Ostar Arriveen PG25" is a mixture of propylene glycol and oat extract manufactured by Canamino, Inc.

Phase A was prepared by heating the propylene glycol to 60°–65° C., adding the polyethylene glycol 8000 and mixing until melted. Behenyl alcohol, stearyl alcohol and stearalkonium chloride are added and mixed until melted. Hydrogenated starch hydrolysate is added and mixed until uniform. Hispagel 200, Lubrasil, or Arriveen PG25 were added (depending on the formulation) and the formulation was mixed until uniform.

Phase B was prepared by mixing dimethicone and myristyl myristate together and heating until uniform. Phase B was added to Phase A slowly under vigorous agitation.

At this point these formulations were ready to use and apply to the surface of a tissue or towel basesheet via rotogravure printing.

Examples 14 and 15 (Invention)

Anti-bacterial formulations having a penetration range of 190 to 220 and a melting point range of 50°–55° C. were prepared having the following compositions:

|   | 14 Wt % | 15 Wt % |
|---|---|---|
| 1) Propylene Glycol | 64.00 | 57.00 |
| 2) MPDiol Glycol | 5.00 | 10.00 |
| 3) Polyethylene Glycol 6000 | 20.00 | 22.00 |
| 4) Stearyl Alcohol | 10.00 | 10.00 |
| 4) Nipacide PX | 1.00 | 1.00 |

The propylene glycol and MPDiol glycol were heated to 60°–60°0 C., adding polyethylene glycol 6000 and stearyl alcohol, and mixing until melted. The Nipacide PX, an anti-bacterial agent manufactured by Nipa Laboratories, was added and mixed until dissolved. These anti-bacterial formulations were added to double re-creped basesheets via rotogravure printing to make a anti-bacterial towel.

The foregoing examples, given for purposes of illustration, are not to be construed as limiting the scope of this invention, which is defined by the following claims and all equivalents thereto.

I claim:

1. A soft tissue or towel product having two outer surfaces, wherein one or both outer surfaces of the product have solidified deposits of a composition comprising from about 30 to about 90 weight percent hydrophilic solvent, from about 10 to about 50 weight percent high molecular weight polyethylene glycol having a molecular weight of about 720 or greater, and from about 5 to about 40 weight percent of a $C_{14}$ to $C_{30}$ fatty alcohol, said composition having a melting point from about 30° C. to about 70° C. and a penetration hardness of from about 5 millimeters to about 360 millimeters.

2. The product of claim 1 wherein the composition is present in an amount of from about 0.5 to about 30 weight percent based on the weight of the product.

3. The product of claim 1 wherein the hydrophilic solvent comprises water.

4. The product of claim 1 wherein the hydrophilic solvent comprises propylene glycol.

5. The product of claim 1 wherein the hydrophilic solvent comprises low molecular weight polyethylene glycol.

6. The product of claim 1 wherein the hydrophilic solvent comprises glycerin.

7. The product of claim 1 wherein the hydrophilic solvent comprises hydrogenated starch hydrolysate.

8. The product of claim 1 wherein the fatty alcohol is cetyl alcohol.

9. The product of claim 1 wherein the fatty alcohol is stearyl alcohol.

10. The product of claim 1 wherein the fatty alcohol is arachidyl alcohol.

11. The product of claim 1 wherein the fatty alcohol is behenyl alcohol.

12. The product of claim 1 wherein the molecular weight of the high molecular weight polyethylene glycol is from about 720 to about 1,840,000.

13. The product of claim 1 wherein the molecular weight of the high molecular weight polyethylene glycol is from about 1400 to about 440,000.

14. A method of making a soft tissue or towel product comprising: (a) heating a composition comprising a hydrophilic solvent, a high molecular weight polyethylene glycol and a fatty alcohol, to a temperature above the melting point of the composition, causing the composition to melt, said composition having a melting point of from about 30° C. to about 70° C.; (b) applying the melted composition to one or both surfaces of a tissue web in spaced-apart deposits; and (c) resolidifying the deposits of the melted composition, said resolidified composition having a penetration hardness of from about 5 to about 360 millimeters.

15. The method of claim 14 wherein the melted composition is applied by printing.

16. A softening composition comprising from about 30 to about 90 weight percent hydrophilic solvent, from about 10 to about 50 weight percent high molecular weight polyethylene glycol having a molecular weight of about 720 or greater, and from about 5 to about 40 weight percent of a $C_{14}$ to $C_{30}$ fatty alcohol, said composition having a melting point from about 30° C. to about 70° C. and a penetration hardness of from about 5 millimeters to about 360 millimeters.

17. The composition of claim 16 comprising one or more hydrophilic solvents selected from the group consisting of water, propylene glycol, low molecular weight polyethylene glycol, glycerin, sorbitol, hydrogenated starch hydrolysate and silicone glycol.

18. The composition of claim 16 wherein the fatty alcohol is selected from the group consisting of cetyl alcohol, stearyl alcohol, arachidyl alcohol and behenyl alcohol.

19. The composition of claim 16 wherein the amount of hydrophilic solvent is from about 40 to about 70 weight percent.

20. The composition of claim 16 wherein the amount of hydrophilic solvent is from about 50 to about 60 percent.

21. The composition of claim 16 wherein the amount of high molecular weight polyethylene glycol is from about 10 to about 30 weight percent.

22. The composition of claim 16 wherein the amount of high molecular weight polyethylene glycol is from about 15 to about 25 weight percent.

23. The composition of claim 16 comprising about 15 weight percent propylene glycol, about 50 weight percent high molecular weight polyethylene glycol, about 10 weight percent cetyl alcohol, and about 25 weight percent hydrogenated starch hydrolysate.

24. The composition of claim 16 comprising about 20 weight percent propylene glycol, about 50 weight percent high molecular weight polyethylene glycol, and about 20 weight percent hydrogenated starch hydrolysate.

25. The composition of claim 16 comprising about 10 weight percent propylene glycol, about 10 weight percent low molecular weight polyethylene glycol, about 50 weight percent high molecular weight polyethylene glycol, about 20 weight percent hydrogenated starch hydrolysate, and about 10 percent dimethicone copolyol.

26. The composition of claim 16 comprising about 55 weight percent propylene glycol, about 20 weight percent high molecular weight polyethylene glycol, and about 20 weight percent stearyl alcohol.

27. The composition of claim 16 comprising about 55 weight percent low molecular weight polyethylene glycol, about 20 weight percent methyl propanediol, about 20 weight percent high molecular weight polyethylene glycol, and about 20 weight percent stearyl alcohol.

28. The composition of claim 16 comprising about 55 weight percent methyl propanediol, about 20 weight percent high molecular weight polyethylene glycol, and about 20 weight percent stearyl alcohol.

29. The composition of claim 16 comprising about 35 weight percent propylene glycol, about 20 weight percent high molecular weight polyethylene glycol, about 10 weight percent behenyl alcohol, about 10 weight percent stearyl alcohol, about 10 weight percent of a mixture of glyceryl and glyceryl polyacrylate, and about 10 weight percent dimethicone.

30. The composition of claim 16 comprising about 30 weight percent propylene glycol, about 15 weight percent high molecular weight polyethylene glycol, about 10 weight percent behenyl alcohol, about 10 weight percent stearyl alcohol, about 15 weight percent hydrogenated starch hydrolysate, about 5 weight percent of a mixture of glyceryl polyacrylate, propylene glycol, cyclomethicone, dimethiconol, and polysorbate 20, and about 10 weight percent dimethicone.

31. The composition of claim 16 comprising about 35 weight percent propylene glycol, about 20 weight percent high molecular weight polyethylene glycol, about 10 weight percent behenyl alcohol, about 10 weight percent stearyl alcohol, about 10 weight percent of a mixture of propylene glycol and oat extract, and about 10 weight percent dimethicone.

32. The composition of claim 16 comprising about 65 weight percent propylene glycol, about 5 weight percent methyl propanediol, about 20 weight percent high molecular weight polyethylene glycol, and about 10 weight percent stearyl alcohol.

33. The composition of claim 16 comprising about 55 weight percent propylene glycol, about 10 weight percent methyl propanediol, about 20 weight percent high molecular weight polyethylene glycol, and about 10 weight percent stearyl alcohol.

* * * * *